(12) United States Patent
Grodzki (10) Patent No.: US 11,150,314 B2
(45) Date of Patent: Oct. 19, 2021

(54) AUTOMATICALLY OPTIMIZED MR IMAGING WITH ULTRA-SHORT ECHO TIMES

(71) Applicant: Siemens Healthcare GmbH, Erlangen (DE)

(72) Inventor: David Grodzki, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/830,951

(22) Filed: Mar. 26, 2020

(65) Prior Publication Data
US 2020/0309881 A1 Oct. 1, 2020

(30) Foreign Application Priority Data
Mar. 26, 2019 (DE) .......................... 102019204151.5

(51) Int. Cl.
| G01R 33/48 | (2006.01) |
| G01R 33/56 | (2006.01) |
| A61B 5/055 | (2006.01) |

(52) U.S. Cl.
CPC ..... *G01R 33/4816* (2013.01); *G01R 33/5602* (2013.01); *G01R 33/5608* (2013.01); *A61B 5/055* (2013.01)

(58) Field of Classification Search
USPC ........................................................ 324/309
See application file for complete search history.

(56) References Cited

U.S. PATENT DOCUMENTS

| 5,910,112 A * | 6/1999 | Judd ...................... A61B 5/055 600/410 |
| 2009/0033328 A1* | 2/2009 | Feiweier ................ G01R 33/58 324/309 |
| 2011/0091090 A1* | 4/2011 | Dahlqvist Leinhard .................... G01R 33/4828 382/131 |
| 2011/0204892 A1* | 8/2011 | Li ........................ G01N 24/081 324/309 |
| 2015/0071514 A1* | 3/2015 | Wang .................... G06T 7/0012 382/131 |
| 2016/0109543 A1 | 4/2016 | Grodzki |

FOREIGN PATENT DOCUMENTS

DE 102014221017 A1 4/2016

OTHER PUBLICATIONS

Google Translation of German Action dated Feb. 4, 2020, Application No. 10 2019 204 151.5 (Year: 2020).*

(Continued)

*Primary Examiner* — Rodney E Fuller
(74) *Attorney, Agent, or Firm* — Schiff Hardin LLP (57) ABSTRACT

Automated setting techniques for MR imaging with ultra-short echo times in a region to be examined are described. With the method protocol parameter values for an MR imaging method are determined. The protocol parameters comprise a predetermined imaging resolution. Optimized values for echo time and bandwidth are also determined based on an image signal simulation, which is based on the determined protocol parameters. The signal to noise ratio and point spread function are used as optimization criteria.

13 Claims, 6 Drawing Sheets

(56) References Cited

OTHER PUBLICATIONS

Grodzki D. M. et al; "Ultrashort Echo Time Imaging Using Pointwise Encoding Time Reduction With Radial Acquisition (PETRA)"; Magnetic Resonance in Medicine; vol. 67; pp. 510-518; 2012.
Rahmer, Jürgen et al: "Three-dimensional radial ultrashort echo-time imaging with T2 adapted sampling"; Magnetic Resonance in Medicine: An Official Journal of the International Society for Magnetic Resonance in Medicine; 2006; 55. Jg.; Nr. 5; pp. 1075-1082.
Wiesinger, Florian et al. "Zero TE MR Bone Imaging in the Head" Magnetic Resonance in Medicine, vol. 75, No. 1, pp. 107-114, Jan. 2016 (First published: Jan. 16, 2015) // https://doi.org/10.1002/mrm.25545;.
Weiger Markus et al., "MRI with Zero Echo Time: Hard versus Sweep Pulse Excitation", in: Magnetic Resonance in Medicine, vol. 66, 2011, pp. 379-389, DOI: 10.1002/mrm.22799.
German Action dated Feb. 4, 2020, Application No. 10 2019 204 151.5.

\* cited by examiner

AUTOMATICALLY OPTIMIZED MR IMAGING WITH ULTRA-SHORT ECHO TIMES

CROSS-REFERENCE TO RELATED APPLICATIONS

The present application claims the benefit of the filing date of German patent application no. 102019204151.5, filed on Mar. 26, 2019, the contents of which are incorporated herein by reference in their entirety.

TECHNICAL FIELD

The disclosure relates to techniques for performing magnetic resonance (MR) imaging using ultra-short echo times.

BACKGROUND

In an MR system, the body to be examined is generally exposed to a relatively powerful main-field magnetic field, of 3 or 7 Tesla for example, with the aid of a main-field magnet system. A gradient system is also used to apply a magnetic field gradient, which determines the magnetic resonance frequency (Larmor frequency) at the respective location. A radio-frequency transmit system is then used to transmit radio-frequency excitation signals (RF pulses) by means of appropriate antenna facilities, with the aim of flipping the nuclear spins of specific atoms excited in a resonant manner by said radio-frequency field (in other words at the Larmor frequency present at the respective location) through a defined flip angle relative to the magnetic field lines of the main magnetic field. Such radio-frequency excitation or the resulting flip angle distribution is also referred to as "magnetization" in the following.

If such an RF pulse acts on spins that are already excited, these can be flipped into another angular position or even returned to an initial state parallel to the main magnetic field. As the excited nuclear spins relax, radio-frequency signals, referred to as magnetic resonance signals, are emitted in a resonant manner, being received by appropriate receive antennas and then further processed. Acquisition of the magnetic resonance signals takes place in the spatial frequency space or "k-space", with the k-space being temporally traversed along a "gradient trajectory" that is defined by the switching of the gradient pulses during measurement, of a slice for example, while the RF pulses are transmitted in a time-coordinated manner. The desired image data can finally be reconstructed from the "raw data" thus acquired by means of a two-dimensional Fourier transform.

Generally predefined pulse sequences determined during measurement, in other words sequences of defined RF pulses as well as gradient pulses in different directions and read-out windows, are used to activate a magnetic resonance tomography system while the receive antennas are switched to receive, and the magnetic resonance signals are received and processed, having been established beforehand in a measurement protocol together with other control data for the measurement.

The relaxation processes resulting during excitation by RF pulses affect both magnetization in the direction of the main magnetic field, as characterized by the T1 relaxation time, and relaxation of the transverse component in the x-y direction, as characterized by the T2 relaxation time. During measurement of component relaxation in the x-y direction it should also be taken into account that the main magnetic field, or B0 magnetic field, has small inhomogeneities, which amplify tissue-specific interactions and contribute to more rapid dephasing and therefore shortening of T2 relaxation. This combined relaxation time is referred to as T2* relaxation time.

To counteract this additional signal degradation, the spins can be synchronized after a certain time or echo time TE by additional RF pulses (180° pulses). Such pulse sequences are referred to as "spin echo" pulse sequences. When this type of pulse sequence is used, the disruptive influence of the magnetic field inhomogeneities is eliminated, and the relaxation of magnetization in the transverse direction takes place more slowly, in other words with T2 relaxation time, which is still only tissue-specific.

In addition to the spin echo sequences there are also what are known as "gradient echo" sequences. These do not require an additional RF pulse. Instead, an artificial magnetic field inhomogeneity is produced by applying a gradient magnetic field. Rapid changes to said gradients result in excitation and rephasing of the spins. Magnetic field inhomogeneities are not compensated for, and therefore the T2* relaxation time is measured.

SUMMARY

In addition to the cited sequence types, which produce an echo by means of RF irradiation or gradient polarity inversion, there are also sequences which measure data directly in Free Induction Decay (FID) after excitation without producing an echo. With such pulse sequences it is possible to acquire signals from body materials, which have extremely short ("ultra-short") TE times, and therefore substances with very short relaxation times or T2* relaxation times can be measured and displayed visually.

Pulse sequences with ultra-short echo times are for example the UTE sequence (UTE=ultra-short echo time), the PETRA sequence (PETRA=point-wise encoding time reduction with radial acquisition) or the zTE sequence (zTE=zero echo time).

Body tissue types that can be displayed in this manner include bones, tendons, ligaments, teeth, and lung tissue. Such body tissue types comprise substances in which powerful covalent bonds are present between the individual atoms. Body parts with the aforementioned body tissue types cannot be displayed visually using conventional MR sequences with longer echo times TE of more than one millisecond, as the excited MR signals have already decayed by the time the echo is produced due to the short relaxation times of the materials of these body parts.

In addition to the visual representation of body structures with the cited body tissue types, MR pulse sequences with ultra-short echo times can also be used to produce what are referred to as µ-maps for MR-PET attenuation correction. The quality of visual representation with the aid of a UTE sequence is a function of different parameters:

For instance, there is a dependence on the type of material of the structure to be displayed. This is essential for the T2 relaxation time or T2* relaxation time, for which the excited MR signal diminishes during the FID (free induction decay) measured in the UTE sequence.

Moreover, there is also a dependence on the echo time TE of the pulse sequence: the minimum echo time $TE_{min}$, which can be used with an MR scanner, is limited by the switching time required to switch between transmit operation and receive operation. A short echo time TE means it is possible to start reading the measurement signal at an earlier time after excitation of the MR signal or during signal decay. The k-space center can therefore be measured with particularly large signal amplitudes for short echo times, resulting in an improved signal to noise ratio (SNR). However, the drop in signal intensity is particularly marked when measuring the outer regions, so the k-space center is weighted particularly significantly compared with the outer regions and therefore unfavorable values are produced for the point spread function (PSF). In other words, higher frequency components of the image information are weighted less for short echo times, resulting in a lower resolution for the image display.

Still further, reading out can be accelerated by an increased read-out bandwidth or an increased read-out gradient strength. It should be noted here that the size of the read-out gradient is proportional to the read-out bandwidth. This can reduce the drop in the amplitude of the read-out signal during reading out, improving the values of the point spread function and therefore improving resolution. However, a higher bandwidth is associated with a reduction in signal to noise ratio.

Conversely, however, a reduction in resolution can reduce the extent of the k-space to be scanned and therefore improve the point spread function. The SNR also has a linear association with the predefined resolution. In other words, a lower predefined resolution improves the SNR, as the shorter scan time means that the k-space can be scanned in the initial phase of signal decay, and therefore with greater signal amplitudes.

The image quality is therefore a function of the three aforementioned variables: required resolution, read-out bandwidth, and selected echo time.

Figure 1:
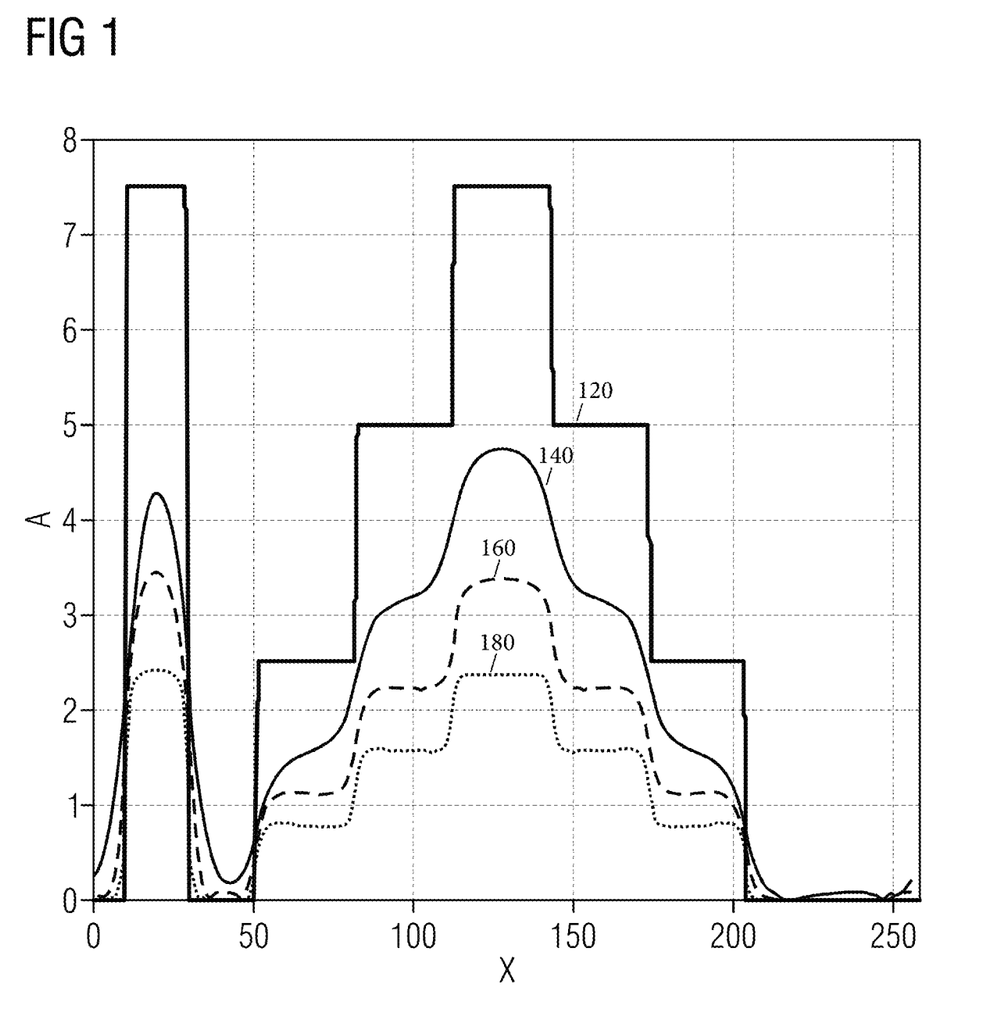
FIG. 1 shows a first diagram of an example MR measurement signal in the spatial space as a function of the location for an echo time of 70 µs and for three different read-out gradient strengths or read-out bandwidths.
Figure 2:
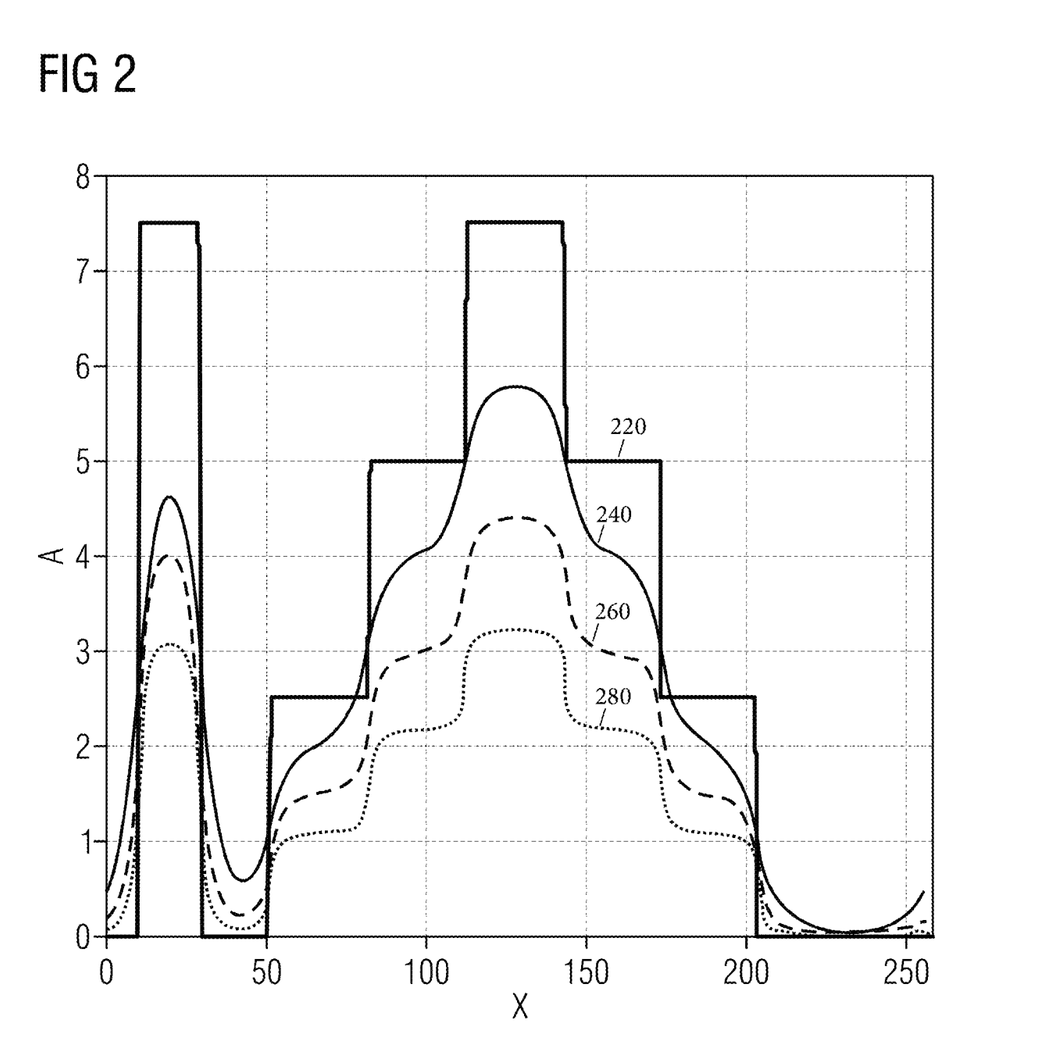
FIG. 2 shows a second diagram of an example MR measurement signal in the spatial space as a function of the location for an echo time of 3 µs and for three different read-out gradient strengths.

FIGS. 1 and 2 show the dependence of image quality on read-out bandwidth and the selected echo time in two diagrams. As can be seen from FIGS. 1 and 2, the optimal pulse sequence parameter values cannot be easily identified beforehand due to the dependence of said values on the T2 relaxation time of the materials in the region to be imaged, and due to the opposing influence of the different pulse sequence parameters on different determination variables of image quality. Generally, therefore, MR imaging protocols with the shortest echo time and read-out bandwidths that are not tailored to the specific situation are conventionally used.

There is therefore the problem of achieving the best possible image quality for MR imaging with an MR pulse sequence with an ultra-short echo time. This problem is addressed by the various embodiments as discussed herein, which include techniques for the automated setting of MR imaging using ultra-short echo times in a region to be examined, which is also described in the claims.

In accordance with the automated setting method for MR imaging using ultra-short echo times in a region to be examined, the protocol parameter values are determined for an MR imaging method. The protocol parameter values to be determined comprise at least one predetermined imaging resolution. These protocol parameter values, for example the resolution, the T2 relaxation time or the T2* relaxation time, or the proton concentration in materials in the region to be imaged, can be predefined or estimated by preliminary examination or based on generally known information about the distribution and properties of the tissue types and substance densities present in the region to be examined Optimized values for echo time and read-out bandwidth may also be determined based on an image signal simulation. Such a simulation is described, for instance, in Grodzki et al., "Ultrashort Echo Time Imaging Using Pointwise Encoding Time Reduction with Radial Acquisition (PETRA)," Magnetic Resonance in Medicine 67:510-518 (2012).

For image signal simulation, the previously-determined protocol parameter values are taken into account, and the SNR and PSF are used as optimization criteria. In other words, a plurality of image signal computer simulations are performed in the region to be examined with different parameter values for echo time and read-out bandwidth, and then after comparison the set of parameter values for echo time and read-out bandwidth, for which the SNR values and the PSF values are optimal (or represent an optimal compromise in respect of image quality requirements), is used. Automated adjustment of both echo time and read-out bandwidth advantageously allows for better image quality to be achieved than with adjustment of echo time alone. Also, the user need not undertake the often non-transparent determination of favorable parameter values for improving image quality, thereby saving time and cost, and also allowing the deployment of less technically-qualified personnel for MR imaging.

With the MR imaging method embodiments, the automated setting method for MR imaging with ultra-short echo times in a region to be examined is first performed. MR imaging then takes place using the determined values for echo time and read-out bandwidth. The MR imaging method performed in accordance with such embodiments achieves better image quality and reduces the outlay required to set protocol parameters prior to performing MR imaging compared with conventional procedures.

In an embodiment, a MR setting apparatus is disclosed. The MR setting apparatus includes a determination unit/circuitry for determining protocol parameter values for an MR imaging method. The protocol parameter values comprise a predetermined resolution for the MR imaging method. The MR setting apparatus also includes an optimization unit/circuitry for determining optimized values for echo time and read-out bandwidth based on an image signal simulation, which is based on the determined protocol parameters. The optimization criteria used in this example include the SNR and the PSF. The embodiments of the MR setting apparatus share the advantages of embodiments of the setting method for MR imaging with ultra-short echo times in a region to be examined.

In an embodiment, an MR imaging system is disclosed that includes a scan unit/circuitry, a control unit/circuitry for activating the scan unit/circuitry with an activation sequence, and an MR setting apparatus. The MR setting apparatus is used to tailor a pulse sequence protocol to specific properties of an examination region to be imaged. The activation sequence run by the control unit/circuitry is based on the pulse sequence adjusted by the MR setting apparatus. The embodiments of the MR imaging system share the advantages of the MR setting apparatus.

In an embodiment, the MR setting apparatus 60 can be part of a user terminal or control facility (e.g. control computer) of a magnetic resonance imaging system, for example. The components of the MR setting apparatus may largely be configured in the form of software components. This is true particularly of the determination unit/circuitry and the optimization unit/circuitry. However, embodiments include some or all of these components additionally or alternatively being implemented in the form of software-assisted hardware, for example FPGAs or the like, particularly when particularly rapid calculations are required. Similarly, the required interfaces can be configured as software interfaces, for example when it is simply necessary to retrieve data from other software components. However, the various components of the MR setting apparatus as described herein can also be configured as interfaces with a hardware-based structure, activated by the appropriate software. For instance, the various components of the MR setting apparatus as discussed herein may be implemented as one or more processing components, which may function as standalone processors or in conjunction with software components, e.g. via execution of machine-readable instructions. Thus, the various components of the MR setting apparatus 60 may alternatively be referred to herein as "determination processing circuitry," "optimization processing circuitry," "scan processing circuitry," control processing circuitry," etc.

A largely software-based implementation has the advantage that control facilities already in use can be retrofitted easily by means of a software update, so that the components operate in accordance with the embodiments as described herein. To this extent, an object of the present disclosure is also achieved by a corresponding computer program product (e.g. a non-transitory computer-readable medium) with a computer program or other suitable computer-readable, executable instructions stored thereon, which can be loaded into a storage facility of a control facility of a magnetic resonance imaging system with program segments for executing the steps of the method embodiments as described herein when the program is run in a suitable control facility. In addition to the computer program, such a computer program product can optionally comprise additional constituent parts, e.g. documentation and/or additional components, as well as hardware components, for example hardware keys (dongles, etc.) for the use of the software.

A machine-readable medium, for example a memory stick, hard disk, or some other transportable or permanently incorporated data carrier can be used for the transfer to the control facility and/or for storage on or in the control facility, the program segments of the computer program that can be read in and executed by a computation unit/circuitry of the control facility being stored thereon. The computation unit/circuitry can have for example one or more interacting microprocessors or the like for this purpose. The computation unit/circuitry can be for example part of a terminal or of the control facility of the magnetic resonance imaging system.

The claims and the description point out advantageous embodiments and developments of the disclosure. The claims of one claim category can also be developed in the same manner as the claims of another claim category. Also, the different features of different embodiments and claims can be combined into new embodiments within the scope of the disclosure.

In one embodiment of the automated setting method for MR imaging with ultra-short echo times in a region to be examined, the determination of the protocol parameter values comprises the following steps:

receiving protocol data, which comprises protocol-based parameter values; and using the protocol-based parameter values as the protocol parameter values to be determined.

Protocol-based parameter values in this context are understood to be parameter values which either result from the constraints of the MR imaging system and the region to be examined (e.g. an estimated T2 relaxation time), or are established beforehand by the user (e.g. the matrix size, field of view (FoV), or a resolution) selected by the user. These parameter values represent localizing parameter values for imaging processes and constraints for simulations. If only this data is used as the basis for the simulation, a simulation can be performed without preliminary measurements based on said parameter values, thereby reducing the outlay for adjusting the pulse sequence.

In one variant of the embodiment of the automated setting method for MR imaging with ultra-short echo times in a region to be examined, a test measurement, in other words MR imaging with low resolution, is performed based on the protocol-based parameter values to determine additional or more precise protocol parameters. For example, the echo time of the test measurement is based on the previously-estimated T2 relaxation time. Test image data is then reconstructed based on raw data acquired during the test measurement. Region-specific image recording parameters are then determined based on the test image data and the region-specific image recording parameters comprising the T2* time and/or the T2 time of the tissue to be imaged. Finally, the region-specific image recording parameters are used additionally or alternatively as the protocol parameter values to be determined. With this embodiment, the simulation can advantageously take place based on more reliable protocol parameter values, so that the result of the simulation or optimization is more reliably and better tailored to specific properties of the region to be examined.

During the test measurement, the relative proton concentration is preferably determined as an additional parameter value and a weighting of the optimization criteria is determined and established as a function of the determined relative proton concentration. The relative proton concentration in this context refers to the concentration of protons in the structure to be imaged relative to its surroundings. With knowledge of the relative proton concentration or proton density, it can advantageously be decided which of the optimization criteria can be weighted more for the simulation.

For example, in the event of a high relative proton concentration in the optimization step (e.g., in excess of a predetermined threshold proton concentration), then the PSF can be weighted more than the SNR, as a good image contrast can then be assumed and the magnitude of the PSF controlling image resolution can be prioritized during the optimization. Conversely, in the event of a low relative proton concentration in the optimization step (e.g., less than a predetermined threshold proton concentration), the SNR can be weighted more than the PSF. Such a scenario results, for example, when imaging the lung. It is expedient here to prioritize optimization of the SNR to show structures with the weak measurable signal at all, if not with high resolution.

In a variant of the embodiment of the automated setting method for MR imaging with ultra-short echo times in a region to be examined, in the optimization step a number of successive image signal simulations may be performed with pulse sequences with different test protocol parameter values. During the image signal simulations, a simulated image signal profile is also determined, and the optimized values of echo time and read-out bandwidth are determined based on the simulated image signal profiles. With this variant, a broad database containing a plurality of simulations can advantageously be used to select the optimal values of echo time and read-out bandwidth, so the optimization operation is extremely precise.

In a variant of the embodiment of the automated setting method for MR imaging with ultra-short echo times in a region to be examined, image signal simulation data relating to simulated image signal profiles, which are assigned to pulse sequences with different test protocol parameter values, are read out from a database and the optimized values are determined based on the simulated image signal profiles. With this variant, there is advantageously no need to perform time-consuming calculations of simulation data at the start of an examination; instead, it is possible to access already-stored simulation data. Such a procedure is expedient when a database has to be accessed quickly for transmission reasons, to save time for the examination.

In a variant of the embodiment of the automated setting method for MR imaging with ultra-short echo times in a region to be examined, values for the optimization criteria are determined based on the simulated image signal profile in each instance. In other words, values are determined for the SNR and the PSF in particular. An optimal value pair is also determined by comparing the determined values, and the test values for echo time and bandwidth assigned to the optimal value pair are established as optimal values. It is advantageously possible to conclude appropriate protocol parameters from the simulated signal data or the image data.

In a variant of the embodiment of the automated setting method for MR imaging with ultra-short echo times in a region to be examined, image signal simulations are performed in the optimization step with pulse sequences of different pulse sequence types and the selection of the most appropriate pulse sequence type is part of the optimization operation. With this variant, it is advantageously possible to search for the pulse sequence type with which the best image quality is achieved for the individual application.

The tested pulse sequences can comprise the following different pulse sequence types, for example: UTE, PETRA, zTE, etc. The UTE sequence comprises a radial scan of the k-space with ultra-short echo times. The PETRA sequence is a combination of individual point scanning in the k-space center and radial acquisition in the k-space outer region. With the zTE sequence, excitation and acquisition of the raw data take place during a constant gradient, so the effective echo time has the value 0.

BRIEF DESCRIPTION OF THE DRAWINGS/FIGURES

The disclosure is described once again in more detail below with reference to the accompanying figures based on exemplary embodiments. In the figures.

DETAILED DESCRIPTION

FIG. 1 and FIG. 2 show the dependence of image quality on the selected echo time and the read-out bandwidth for a UTE pulse sequence.

FIG. 1 shows an example MR measurement signal in the spatial space for a first echo time TE as a function of the location for an echo time of 70 µs and three different read-out gradient strengths or read-out bandwidths. In the diagram, the signal amplitude 'A' is shown as a function of the location 'x,' with an echo time TE of 70 µs. Signal lines for different read-out gradient strengths are hatched differently (i.e. with different line styles). A thick continuous line (120) represents the rectangular or stepped structure of the objects themselves. A thinner continuous curved line (140) represents the read-out signal for a read-out gradient strength of 5 mT/m. A broken line (160) shows the read-out signal for a read-out gradient strength of 10 mT/m. A dotted line (180) shows the read-out signal for a read-out gradient strength of 20 mT/m.

FIG. 2 shows the signal amplitude A as a function of the location x with an echo time TE of 3 µs. In FIG. 2, a rectangular or stepped structure shown by a thick line (220) represents the objects themselves. A somewhat thinner continuous curved line (240) represents the read-out signal for a read-out gradient strength of 5 mT/m. A broken line (260) shows the read-out signal for a read-out gradient strength of 10 mT/m. A dotted line (280) shows the read-out signal for a read-out gradient strength of 20 mT/m.

As can be seen from a comparison of the two diagrams in FIG. 1 and FIG. 2, a greater amplitude of the measurement signal, and therefore a better SNR, result with shorter echo times and the same read-out gradient strength. Conversely, with the longer echo time TE of 70 µs, the resolution achieved is higher than with the shorter echo time TE of 3 µs for the same read-out gradients. This is because the signal amplitude for the same read-out gradient strengths between two structures (around x=30 to 50) in FIG. 1 is much lower than in FIG. 2. As shown by the differently hatched lines for signal amplitude, the resolution with higher gradient strength or read-out bandwidth is better than with lower gradient strength, as with a higher gradient strength the k-space can be scanned more rapidly and therefore the drop in signal amplitude during reading out is less marked. In the example, shown in FIG. 1 and FIG. 2 an optimal compromise between SNR and PSF would be achieved for an echo time of 3 µs at 20 mT/m, and for an echo time of 70 µs at 10 mT/m.

Figure 3:
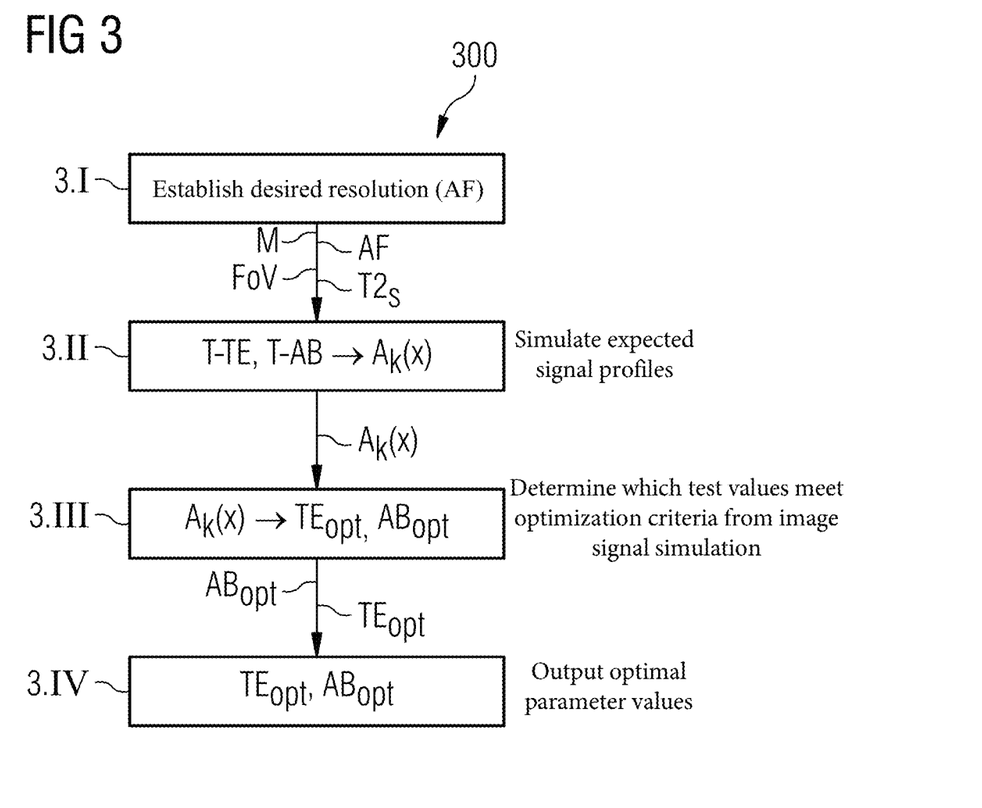
FIG. 3 shows a flow diagram of an example automated setting method for MR imaging with ultra-short echo times in a region to be examined, according to a first exemplary embodiment of the disclosure.

FIG. 3 shows a flow diagram 300 of an example automated setting method for MR imaging with ultra-short echo times in a region to be examined according to a first exemplary embodiment of the disclosure.

In step 3.I, a desired resolution AF is first established. A matrix size M and FOV (Field of View) are specified by the user for this purpose.

In step 3.I, the approximate T2 time or T2* time T2s of the tissue to be imaged is estimated. Lung tissue, for example, has a different T2 time from bone tissue. The type of tissue to be imaged is normally known, so the T2 relaxation time can be estimated based on this knowledge.

Then in step 3.II, a simulation of the expected signal profiles Ak(x) (k is a natural number) takes place for different combinations of test parameter values for echo time TE and read-out bandwidth AB based on the estimated parameter T2s, in other words the T2* relaxation time or the T2 relaxation time. For example, a simulation takes place step-by-step for values T-TE of echo time, starting from the minimum echo time $TE_{min}$ of the MR system up to the T2 relaxation time or T2* relaxation time of the tissue to be imaged. Parameter values T-AB of 100 Hz/Pixel to 1000 Hz/Pixel, for example, are used in 100 Hz/Pixel steps for the read-out bandwidth for successive simulations.

Then in step 3.III, it is determined, based on the image signal simulation, which of the test parameter values T-TE, T-AB results in an optimal compromise between the two optimization criteria, which comprise a high SNR and a favorable profile for the PSF, and in step 3.IV the most favorable parameter values TEopt, ABopt are output as result values. These optimal parameter values TEopt, ABopt can then be used by a control facility or in a terminal of an MR system to adjust a pulse sequence for MR imaging. Automated determination of the factors characterizing image quality, in other words the SNR and the PSF, is limited to image regions in which the substance or tissue to be imaged with a defined T2 time is located.

Figure 4:
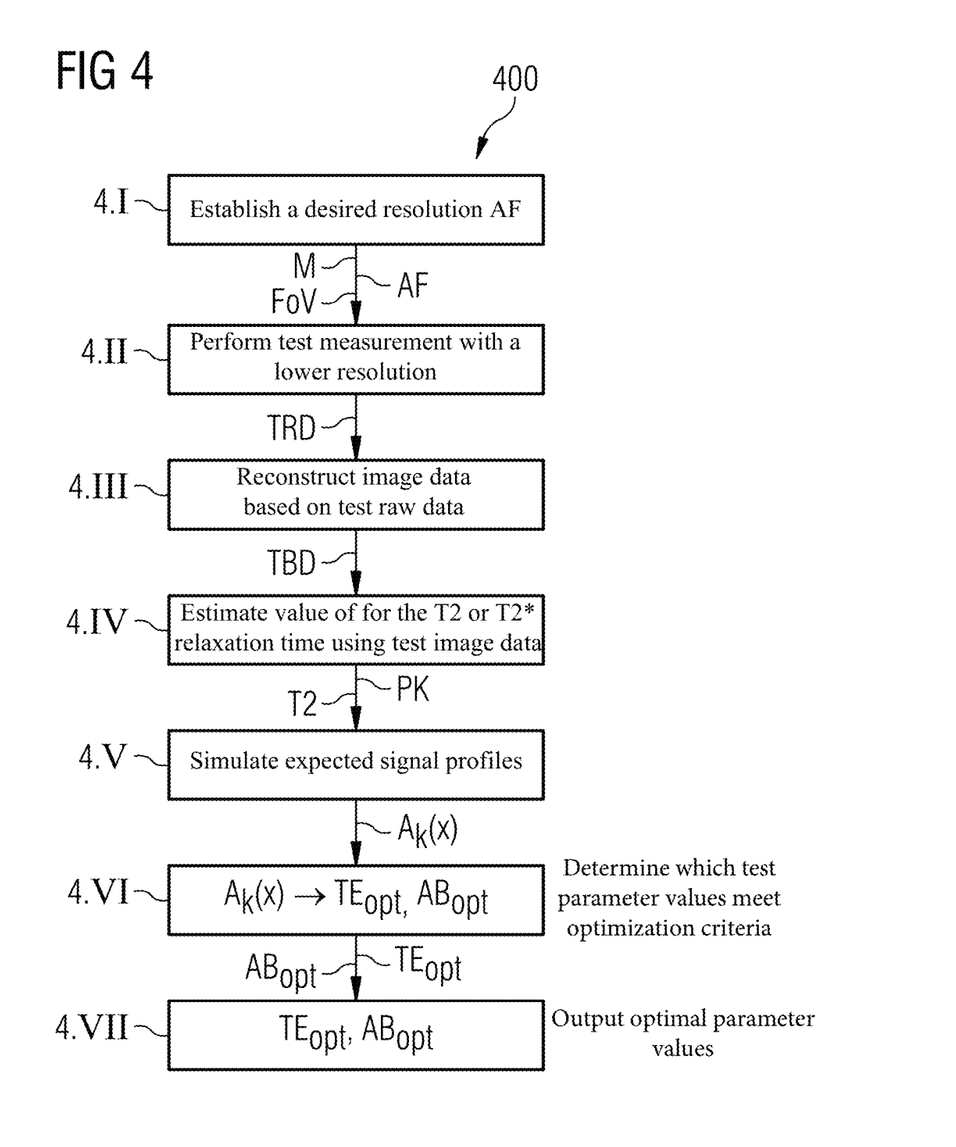
FIG. 4 shows a flow diagram of an example automated setting method for MR imaging with ultra-short echo times in a region to be examined, according to a second exemplary embodiment of the disclosure.

FIG. 4 shows a flow diagram 400 of an example automated setting method for MR imaging with ultra-short echo times in a region to be examined according to a second exemplary embodiment of the disclosure.

In step 4.I, a desired resolution AF is first established based on a matrix size M and a field of view FoV.

Then in step 4.II, a test measurement is performed in the region to be examined with a lower resolution, in other words a resolution significantly below the desired resolution AF. Test raw data TRD is acquired from the region to be examined in this process. In step 4.III, test image data TBD is reconstructed based on the test raw data TRD.

In step 4.IV, a value T2 for the T2* relaxation time or T2 relaxation time of the tissue to be imaged is also estimated based on the test image data TBD. An estimation of the proton concentration PK of the tissue to be imaged compared with the surrounding tissue also takes place based on the measured signal amplitude A.

In step 4.V, expected signal profiles Ak(x) (k is a natural number) are simulated for different combinations of test parameter values for echo time TE and read-out bandwidth AB based on the localizing parameters T2, PK, in other words the T2* relaxation time or T2 relaxation time and the proton concentration. For example, a step-by-step simulation takes place for echo time values, starting from the minimum echo time $TE_{min}$ of the MR system up to the T2 relaxation time or T2* relaxation time of the tissue to be imaged. Parameter values of 100 Hz/Pixel to 1000 Hz/Pixel, for example, are used in 100 Hz/Pixel steps for the read-out bandwidth for successive simulations.

In step 4.VI, it is then determined based on the image signal simulation Ak(x) which of the test parameter values T-TE, T-AB results in an optimal compromise between the two optimization criteria, which comprise a high SNR and a favorable profile for the PSF. During this determination, the two optimization criteria can be weighted appropriately as a function of the proton concentration PK determined in step 4.III. For example, when there is a high signal-emitting proton density PK in the region to be examined, as is the case when imaging tendons or ligaments, the PSF criterion is weighted more than the SNR criterion, as this means the image signal will be strong anyway. Otherwise, when a low value for proton density PK is determined in step 4.III, as is the case for example when lung tissue is imaged, the SNR criterion should be weighted more, to display the less measurable image signal, not so sharply but with sufficient contrast in relation to the background noise, and in step 4.VII the most favorable parameter values TEopt, ABopt are output as result values.

Figures 5, 6:
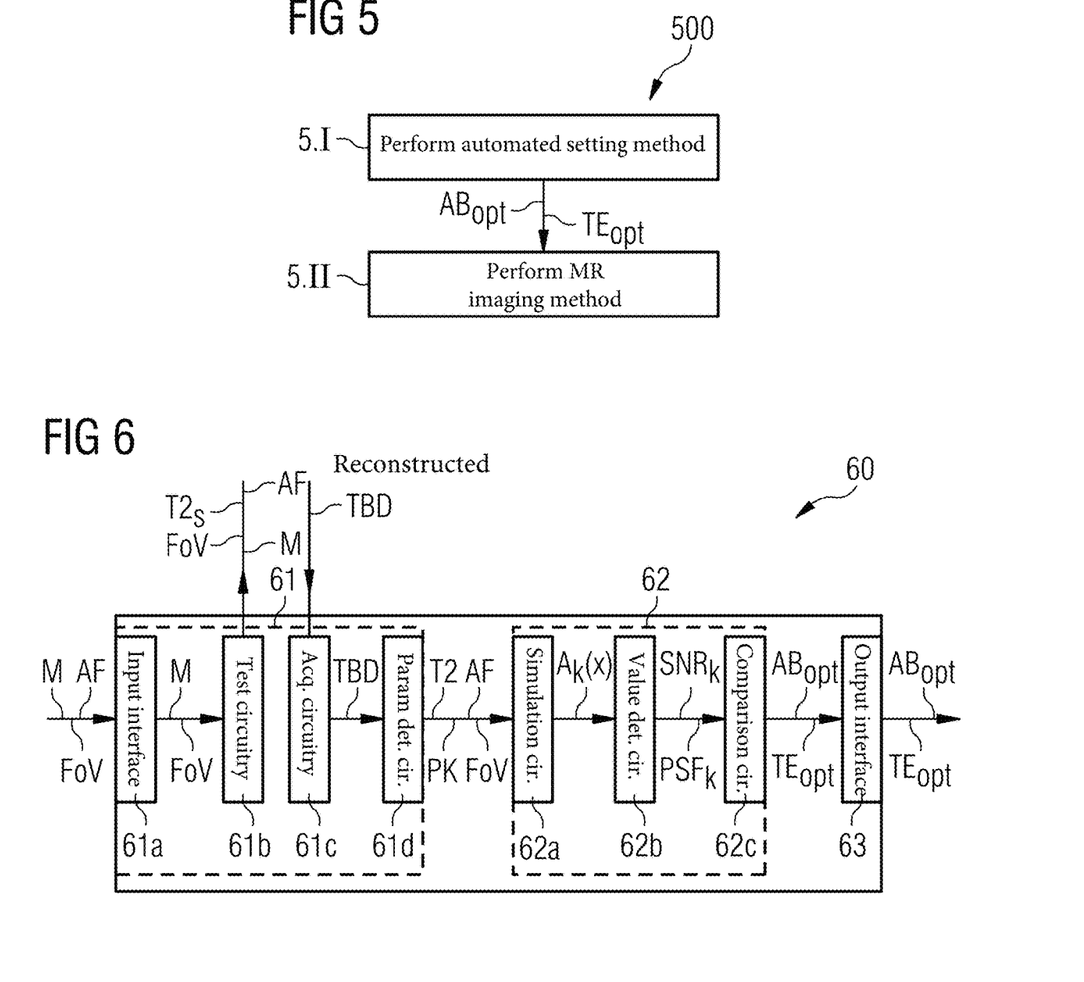
FIG. 5 shows a flow diagram of an example imaging method according to an exemplary embodiment of the disclosure.
FIG. 6 shows a schematic view of an example MR setting apparatus, according to an exemplary embodiment of the disclosure.

FIG. 5 shows a flow diagram 500 of an example imaging method according to an exemplary embodiment of the disclosure. In step 5.I, an automated setting method is performed, as shown in FIG. 3 and FIG. 4. Then, in step 5.II, an MR imaging method is performed using an MR pulse sequence with the optimal sequence parameters determined in step 5.I, in other words in particular the result values TEopt, ABopt.

FIG. 6 shows a schematic view of an example MR setting apparatus 60 according to an exemplary embodiment of the disclosure. Part of the MR setting apparatus 60 is a determination unit/circuitry 61 for determining protocol parameter values M, FoV, T2s, T2, PK for an MR imaging method. The determination unit/circuitry 61 has an input interface 61a, which receives information input by the user relating to the field of view FoV and the matrix size M, from which the desired resolution AF results. The determination unit/circuitry 61 also has a test unit/circuitry 61b for performing a test measurement with low resolution. To this end the test unit/circuitry 61b sends test pulse sequence parameters T2s, AF, M to a control facility (e.g. a control computer) of an MR system (see FIG. 7), which then runs a pulse sequence based on the test pulse sequence parameters T2s, AF, M.

Part of the determination unit/circuitry 61 is also an image data acquisition unit/circuitry 61c, which receives reconstructed test image data TBD from a reconstruction unit/circuitry (see FIG. 7) of the control facility of the MR system, which has been reconstructed based on raw data TRD acquired during the test measurement. The determined test image data TBD is sent to a parameter determination unit/circuitry 61d, which is also part of the determination unit/circuitry 61. The parameter determination unit/circuitry 61d is designed to determine region-specific image recording parameters T2, PK based on the test image data TBD. The region-specific image recording parameters T2, PK comprise the T2* time and/or the T2 time of the tissue to be imaged and the proton concentration PK of the region to be examined.

The protocol parameter values M, FoV, AF, T2, PK determined by the determination unit/circuitry 61 are sent to an optimization unit/circuitry 62, which is also part of the MR setting apparatus 60. The optimization unit/circuitry 62 serves to determine optimized values TEopt, ABopt for echo time and bandwidth based on an image signal simulation, which is based on the determined protocol parameters AF, M, FoV, T2, PK.

To this end the optimization unit/circuitry 62 has a simulation unit/circuitry 62a, which can be used to perform several successive image signal simulations with pulse sequences with different test protocol parameter values TEtest, ABtest. Such a simulation unit/circuitry has a computation unit/circuitry, on which a simulation program is run, which calculates an image signal profile Ak(x) based on the input test protocol parameter values TEtest, ABtest and the determined protocol parameter values AF, M, FoV, T2, PK. The simulation unit/circuitry 61a performs a number N of image signal simulations based on the different test protocol parameter values TEtest, ABtest, a simulated image signal profile Ak(x) being determined in each instance (k=1, N, N is a natural number). The determined image signal profiles Ak(x) are sent to a value determination unit 62b, which in each instance determines a value pair of values SNRk, PSFk of the optimization criteria, in other words the SNR and the PSF, based on the simulated image signal profiles Ak(x). The SNR results from the ratio of the amplitude of background noise to signal amplitude.

The point spread function (PSF) yields, in accordance with Equation 1 below, as follows:

$$PSF = iFFT\left(e^{-\frac{t_c(x_k)}{T_2}}\right), \quad \text{Eqn. 1}$$

where iFFT is the inverse (fast) Fourier transform, and $t_c(x_k)$ represents the coding time of the k-space point $x_k$, and T2 is the T2 relaxation time. The argument gives the factor by how much the signal has already decayed at which k-space point.

The determined value pairs are sent to a comparison unit/circuitry 62c, which determines an optimal value pair SNRopt, PSFopt by means of a weighted comparison and establishes the test values TEtest, ABtest for echo time TE and bandwidth AB assigned to the optimal value pair as optimal values TEopt, ABopt. In other words, the test values TEtest, ABtest are said to be optimized by meeting optimization criteria in accordance with a defined or predetermined SNR and PSF. The comparative weights can be established based on the determined proton density PK. The result values TEtest, ABtest are finally output by way of an output interface 63, which is also part of the MR setting apparatus 60.

Figure 7:
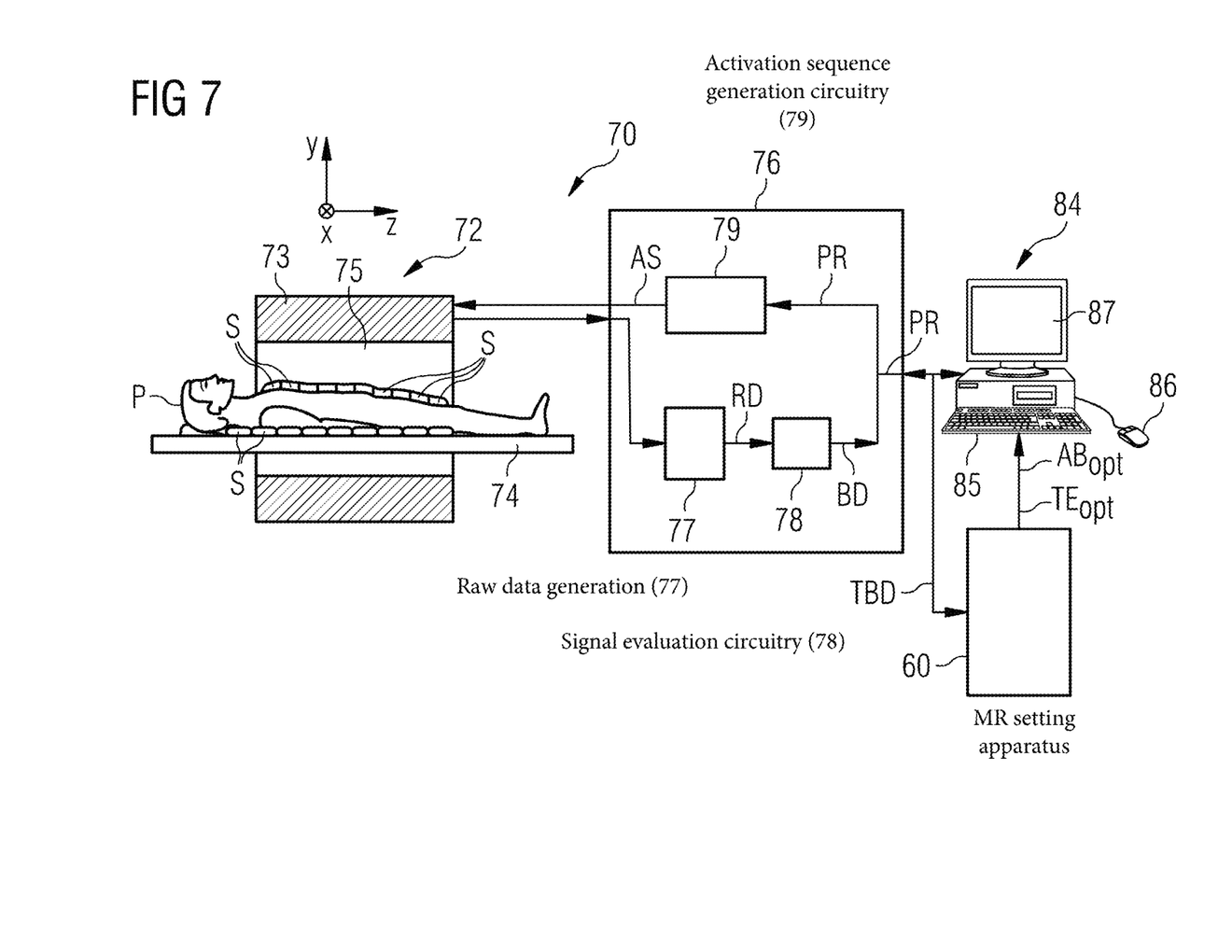
FIG. 7 shows a schematic view of an example MR system, according to an exemplary embodiment of the disclosure.

FIG. 7 shows a schematic view of an example MR system 70 according to an exemplary embodiment of the disclosure. FIG. 7 shows an exemplary embodiment of an MR system 70, which is able to operate according to the methods as shown in FIG. 3 to FIG. 5, for instance. The core of this MR system 70 is the magnetic resonance tomography unit/circuitry 72 itself, in which a patient P is positioned on a patient support table 74 (also referred to as a couch 74) in a circular main-field magnet 73, which encloses the measurement space 75. A plurality of local coils S, also referred to as magnetic resonance coils, for example are located on and optionally also below the patient.

The couch 74 can be moved in the longitudinal direction, in other words along the longitudinal axis of the tomography unit 72. This direction is referred to as the z-direction in the spatial coordinates system, which is also shown. Located within the main-field magnet in the tomography unit 72 is a whole body coil (not shown in detail), which can be used to transmit and receive radio-frequency pulses. The tomography unit 72 also has gradient coils in the usual manner (not shown in FIG. 7), in order to be able to apply a magnetic field gradient in each of the spatial directions x, y, z.

The tomography unit/circuitry 72 is activated by a control computer 76, shown separately here. A terminal 84 is connected to the control computer 76. Said terminal 84 has a screen 87, a keyboard 85 and a pointing device 86 for a graphical user interface, for example a mouse 86 or the like. The terminal 84 serves inter alia as a user interface, by way of which an operator operates the control computer 76 and thus the tomography unit/circuitry 72. Both (or either) of the control computer 76 and the terminal 84 can be integral parts of the tomography unit/circuitry 72.

The MR system 70 can also have all further standard components or features of such systems, for example interfaces for connecting a communication network, for example an image information system or the like. No such components are however shown in FIG. 7 for greater clarity.

An operator can communicate with the control computer 76 by way of the terminal 84, thereby ensuring the desired measurements are performed, in that for example the tomography unit/circuitry 72 is activated by the control computer 76 so that the required radio-frequency pulse sequences are transmitted by the radio-frequency coils and the gradient coils are switched appropriately. The raw data RD required for imaging and coming from the tomography unit/circuitry is acquired by way of the control computer 76. To this end the control computer 76 has a raw data generation unit/circuitry 77, in which measurement signals coming from the tomography unit/circuitry 72 are converted to raw data RD.

This is done for example by digitizing the measurement signals. Raw data RD is reconstructed to produce image data BD in a signal evaluation unit/circuitry 78, also referred to as a reconstruction unit/circuitry, which can be for example a module of the control computer 76. The image data BD can be visualized for example on the screen 87 of the terminal 84 and/or stored in a memory or sent by way of a network. The control computer 76 also has an activation sequence generation unit/circuitry 79, which is used to generate an activation sequence AS according to a protocol PR, which is received for example from the terminal 84.

For example, the activation sequence generation unit/circuitry 79 receives protocol data PR, comprising predetermined parameter values TE, AB of a pulse sequence AS to be determined, from the terminal 84. The activation sequence generation unit/circuitry 79 is also designed to run an activation sequence AS on the magnetic resonance tomography unit/circuitry 72.

The MR system 70 shown in FIG. 7 also comprises am MR setting apparatus 60. The MR setting apparatus 60 is designed to determine optimized protocol parameters TEopt, ABopt in the manner shown in FIG. 3 to FIG. 4.

The determined optimal protocol parameter values TEopt, ABopt are then sent to the terminal 84. In the terminal 84 the optimal protocol parameter values TEopt, ABopt are taken into account when producing a protocol PR, which is sent to the control computer 76 upon completion. As mentioned above, the control computer 76 comprises an activation sequence generation unit/circuitry 79, which receives the protocol data PR comprising the determined parameter values TEopt, ABopt of a pulse sequence AS from the terminal 84. The generated activation sequence AS is then run on the magnetic resonance tomography unit/circuitry 72 with the aid of the activation sequence generation unit/circuitry 79 and the actual image recording can be performed with the activation sequence AS tailored to the determined parameter values TEopt, ABopt.

At least some or even all of the components of the MR setting apparatus 60 required to implement the embodiments as described herein in a MR system 70, for example the determination unit/circuitry 61 and the optimization unit/circuitry 62, can be provided in the form of software components. For example the MR setting apparatus 60 can also be part of the control computer 76 and comprise the activation sequence generation facility 79. Standard magnetic resonance systems generally have programmable control facilities anyway, so the embodiments can preferably be realized in this manner with the aid of appropriate control software. In other words, a corresponding computer program may be loaded into the memory (e.g. a non-transitory computer-readable medium) of a programmable control facility 76 of the MR system 70 in question, said computer program having program code means for performing the setting method embodiments by the MR system 70 as discussed herein. This allows existing magnetic resonance systems to be retrofitted simply and economically.

In particular it is possible for some of the components also to be realized as subroutines in components already present in the control facility 76 or for components already present also to be used to facilitate the functionality of the embodiments as described herein.

In closing, it should be noted once again that the methods and apparatuses described above are merely preferred exemplary embodiments of the disclosure and the embodiments can be varied by the person skilled in the art without departing from the scope of the disclosure. For the sake of completeness, it should also be noted that the use of the indefinite article "a" or "an" does not exclude the possibility of the features in question also being present in multiples. Similarly the term "unit" does not exclude this also comprising a number of components, which can optionally also be spatially distributed.

What is claimed is:

1. A method for performing magnetic resonance (MR) imaging using ultrashort echo times in a region to be examined, comprising:
   determining protocol parameter values for performing MR imaging, the protocol parameter values being associated with a predetermined MR imaging resolution;
   determining values for echo time and bandwidth based on an image signal simulation that uses the determined protocol parameter values, wherein the determined echo time and bandwidth values meet an optimization criteria based upon signal to noise ratio (SNR) values and point spread function (PSF) values; and
   performing MR imaging using an activation sequence that is based upon the determined echo time and bandwidth values.

2. The method as claimed in claim 1, wherein the determination of the protocol parameter values comprises:
   receiving protocol data including protocol-based parameter values; and
   using the received protocol-based parameter values to determine the protocol parameter values.

3. The method as claimed in claim 2, wherein the determination of the protocol parameter values comprises:
   performing a test measurement with low resolution based on the received protocol-based parameter values;
   reconstructing test image data based on raw data acquired during the test measurement;
   determining region-specific image recording parameters based on the test image data, the region-specific image recording parameters including at least one of a T2* relaxation time and a T2 relaxation time of tissue to be imaged; and
   using the region-specific image recording parameters to determine the protocol parameter values.

4. The method as claimed in claim 3, further comprising:
   determining, during the test measurement, a relative proton concentration as an additional parameter value; and
   determining a weighting of the optimization criteria as a function of the determined relative proton concentration.

5. The method as claimed in claim 4, wherein the determining of the weighting of the optimization criteria includes weighting the PSF values more than the SNR values when relative proton concentration exceeds a threshold proton concentration value.

6. The method as claimed in claim 4, wherein the determining of the weighting of the optimization criteria includes weighting the SNR values more than the PSF values when relative proton concentration is less than a threshold proton concentration value.

7. The method as claimed in claim 1, further comprising:
   performing a number of successive image signal simulations using pulse sequences having different test protocol parameter values; and
   determining, during each of the image signal simulations, a respective simulated image signal profile, and
   wherein determining the values for echo time and bandwidth comprises determining the values for echo time and bandwidth based on each respective simulated image signal profile.

8. The method as claimed in claim 7, further comprising:
   determining the SNR values and the PSF values based on each respective simulated image signal profile;
   determining an optimal value pair of the SNR values and the PSF values by comparing the determined SNR values and the PSF values resulting from each respective simulated image signal profile; and
   determining the values for echo time and bandwidth as test protocol parameter values corresponding to an echo time and bandwidth matching the optimal value pair of the SNR values and the PSF values.

9. The method as claimed in claim 1, further comprising:
   reading out, from a database, image signal simulation data relating to simulated image signal profiles, which are assigned to pulse sequences with different test protocol parameter values, and
   wherein determining the values for echo time and bandwidth comprises determining the values for echo time and bandwidth based on the simulated image signal profiles.

10. The method as claimed in claim 1, wherein the image signal simulations are performed using pulse sequences of different pulse sequence types.

11. The method as claimed in claim 10, wherein the different pulse sequence types comprise one or more of an ultra-short echo time (UTE) sequence, a point-wise encoding time reduction with radial acquisition (PETRA) sequence, and a zero echo time (zTE) sequence.

12. A magnetic resonance setting (MR) apparatus, comprising:
   determination processing circuitry configured to determine protocol parameter values for performing MR imaging, the protocol parameter values being associated with a predetermined MR imaging resolution;
   optimization processing circuitry configured to determine values for echo time and bandwidth based on an image signal simulation that uses the determined protocol parameter values,
   wherein the determined echo time and bandwidth values meet an optimization criteria that is based upon signal to noise ratio (SNR) values and point spread function (PSF) values; and
   scan processing circuitry configured to perform MR imaging using an activation sequence that is based upon the determined echo time and bandwidth values.

13. A non-transitory computer-readable medium having instructions stored thereon that, when executed by one or more processors of a magnetic resonance system, cause the magnetic resonance system to:
   determine protocol parameter values for performing MR imaging, the protocol parameter values being associated with a predetermined MR imaging resolution;
   determine values for echo time and bandwidth based on an image signal simulation that uses the determined protocol parameter values,
   wherein the determined echo time and bandwidth values meet an optimization criteria that is based upon signal to noise ratio (SNR) values and point spread function (PSF) values; and
   perform MR imaging using an activation sequence that is based upon the determined echo time and bandwidth values.

* * * * *